United States Patent
Chopra et al.

(10) Patent No.: US 8,940,935 B2
(45) Date of Patent: Jan. 27, 2015

(54) BIS-UREA GELATORS FOR CURABLE INK APPLICATIONS

(71) Applicant: Xerox Corporation, Norwalk, CT (US)

(72) Inventors: Naveen Chopra, Oakville (CA); Michelle N. Chretien, Mississauga (CA); Barkev Keoshkerian, Thornhill (CA); Jenny Eliyahu, Maple (CA); Daryl W. Vanbesien, Burlington (CA); Adela Goredema, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 13/752,134

(22) Filed: Jan. 28, 2013

(65) Prior Publication Data

US 2014/0213820 A1    Jul. 31, 2014

(51) Int. Cl.
    *C07C 275/26*    (2006.01)

(52) U.S. Cl.
    CPC .................................. *C07C 275/26* (2013.01)
    USPC .................................. 564/57; 564/54; 564/58

(58) Field of Classification Search
    USPC .............................................. 564/54, 58, 57
    See application file for complete search history.

(56) References Cited

U.S. PATENT DOCUMENTS

| | | | |
|---|---|---|---|
| 3,812,160 A * | 5/1974 | Teach | 549/493 |
| 6,471,758 B1 * | 10/2002 | Kelderman et al. | 106/31.29 |
| 7,153,349 B2 | 12/2006 | Carlini et al. | |
| 7,259,275 B2 | 8/2007 | Belelie et al. | |
| 7,270,408 B2 | 9/2007 | Odell et al. | |
| 7,271,284 B2 | 9/2007 | Toma et al. | |
| 7,276,614 B2 | 10/2007 | Toma et al. | |
| 7,279,506 B2 | 10/2007 | Sisler et al. | |
| 7,279,587 B2 | 10/2007 | Odell et al. | |
| 7,293,868 B2 | 11/2007 | Odell et al. | |
| 7,317,122 B2 | 1/2008 | Carlini et al. | |
| 7,323,498 B2 | 1/2008 | Belelie et al. | |
| 7,384,463 B2 | 6/2008 | Norsten et al. | |
| 7,449,515 B2 | 11/2008 | Belelie et al. | |
| 7,459,014 B2 | 12/2008 | Breton et al. | |
| 7,531,582 B2 | 5/2009 | Toma et al. | |
| 7,538,145 B2 | 5/2009 | Belelie et al. | |
| 7,541,406 B2 | 6/2009 | Banning et al. | |
| 7,553,011 B2 | 6/2009 | Odell et al. | |
| 7,556,844 B2 | 7/2009 | Iftime et al. | |
| 7,559,639 B2 | 7/2009 | Belelie et al. | |
| 7,560,587 B2 | 7/2009 | Goredema et al. | |
| 7,563,489 B2 | 7/2009 | Carlini et al. | |
| 7,578,587 B2 | 8/2009 | Belelie et al. | |
| 7,625,956 B2 | 12/2009 | Odell et al. | |
| 7,632,546 B2 | 12/2009 | Odell et al. | |
| 7,674,842 B2 | 3/2010 | Belelie et al. | |
| 7,681,966 B2 | 3/2010 | Parker et al. | |
| 7,683,102 B2 | 3/2010 | Odell et al. | |
| 7,690,782 B2 | 4/2010 | Odell | |
| 7,691,920 B2 | 4/2010 | Belelie et al. | |
| 7,699,922 B2 | 4/2010 | Breton et al. | |
| 7,714,040 B2 | 5/2010 | Toma et al. | |
| 7,754,779 B2 | 7/2010 | Odell et al. | |
| 7,812,064 B2 | 10/2010 | Odell et al. | |
| 7,820,731 B2 | 10/2010 | Odell et al. | |

FOREIGN PATENT DOCUMENTS

| | | | | |
|---|---|---|---|---|
| EP | 0816449 | * | 1/1998 | ............. C09D 11/00 |
| EP | 1174461 | * | 1/2002 | ........... C08K 5/3462 |
| EP | 2254126 | * | 5/2009 | ............... H01B 3/00 |

OTHER PUBLICATIONS van Esch, et al. "Self-assembly of Bisurea Compounds in Organic Solvents and on Solid Substrates," Chem. Eur. J., 3(8), 1997.*
de Feyter, et al. "Supramolecular Control of Two-Dimensional Phase Behavior," Chem. Eur. J., 9(5), 2003.*
CAS Reg. No. 109661-36-1, CAS Registry Database, Entered in STN Aug. 8, 1987.*
STN Database, CAS Registry, CAS No. 312930-49-7, entered in STN Jan. 5, 2001.*
STN Database, CAS Registry, CAS No. 341929-87-1, entered in STN Jun. 17, 2001.*

* cited by examiner

*Primary Examiner* — Paul A Zucker
*Assistant Examiner* — Mark Luderer
(74) *Attorney, Agent, or Firm* — Pillsbury Winthrop Shaw Pittman LLP

(57) ABSTRACT

The disclosure provides curable inks including a bis-urea gelator having the structure of Formula I.

$$R_1-\underset{H}{N}-\overset{O}{\overset{\|}{C}}-\underset{H}{N}-X-\underset{H}{N}-\overset{O}{\overset{\|}{C}}-\underset{H}{N}-R_1'$$

Formula I wherein R and R' each, independently of the other, is a saturated aliphatic hydrocarbon group selected from the group consisting of (1) linear aliphatic groups, (2) branched aliphatic groups, (3) cyclic aliphatic groups, (4) aliphatic groups containing both cyclic and acyclic portions, any carbon atom of the saturated aliphatic hydrocarbon group may be optionally substituted with an alkyl group (cyclic or acyclic), wherein (1) and (2) groups have a carbon number of from about 1 to about 22 carbons, and wherein (3) and (4) groups have a carbon number of from about 4 to about 10 carbons; and X is selected from the group consisting of: (i) an alkylene group, (ii) an arylene group, (iii) an arylalkylene group, and (iv) an alkylarylene group.

12 Claims, 1 Drawing Sheet

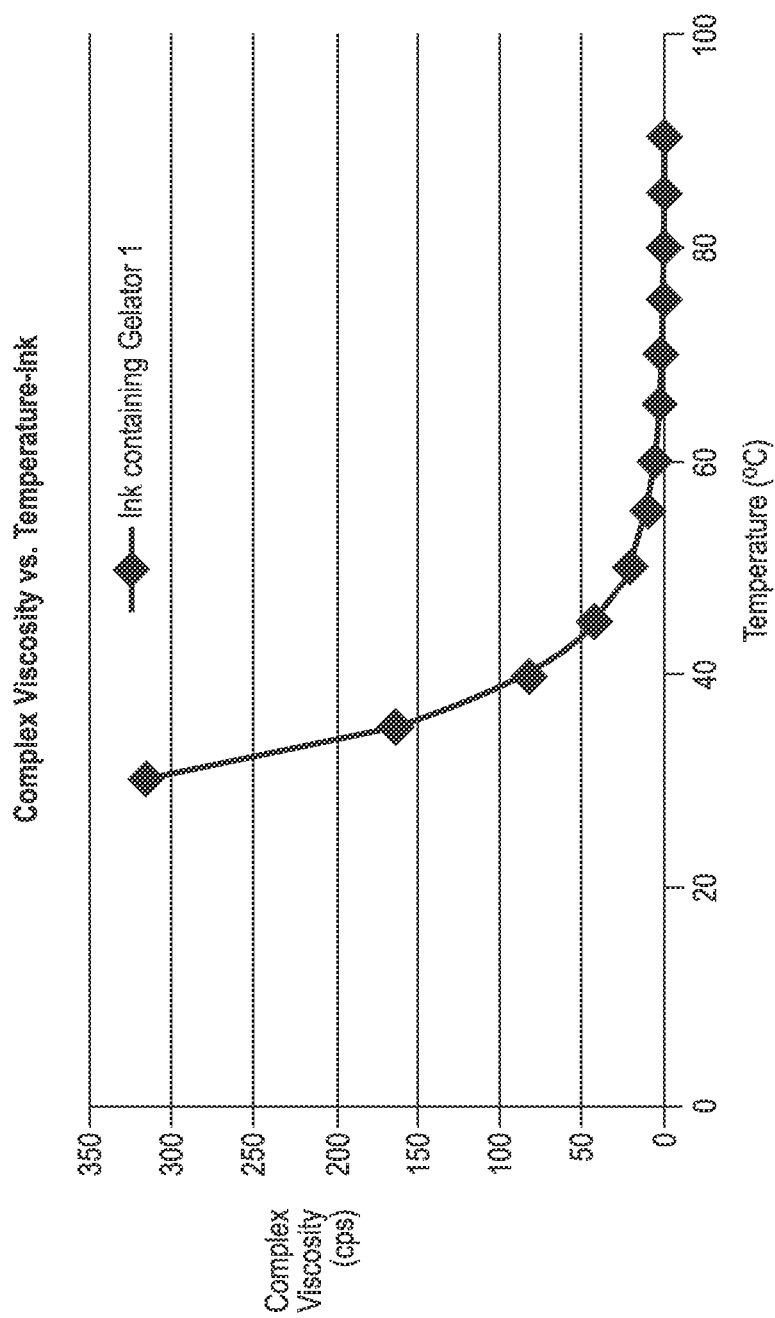

BIS-UREA GELATORS FOR CURABLE INK APPLICATIONS

CROSS REFERENCE TO RELATED APPLICATIONS

Reference is made to commonly owned and co-pending, U.S. patent application Ser. No. 13/752,191 entitled "Ultraviolet Curable Inks Comprising Bis-Urea Gelators" to Chopra et al. filed electronically on the same day as the present application, the entire disclosures of which is incorporated herein by reference in its entirety.

BACKGROUND

The present embodiments are directed to curable inks, such as e-beam curable inks and ultraviolet (UV) curable inks. Curable inks generally include at least one curable monomer, a colorant, and a radiation activated initiator that initiates polymerization of curable components of the ink. In particular, the curable ink is an UV curable gel ink. More specifically, the curable ink is an UV curable ink including a gelator. These UV curable gel ink compositions can be used for ink jet printing in a variety of applications.

UV curable gel inks are known. They are for example disclosed in, for example, U.S. Pat. Nos. 7,153,349, 7,259,275, 7,270,408, 7,271,284, 7,276,614, 7,279,506, 7,279,587, 7,293,868, 7,317,122, 7,323,498, 7,384,463, 7,449,515, 7,459,014, 7,531,582, 7,538,145, 7,541,406, 7,553,011, 7,556,844, 7,559,639, 7,563,489, 7,578,587, 7,625,956, 7,632,546, 7,674,842, 7,681,966, 7,683,102, 7,690,782, 7,691,920, 7,699,922, 7,714,040, 7,754,779, 7,812,064, and 7,820,731, the disclosures of each of which are totally incorporated herein by reference. UV curable gel inks can exhibit desirable characteristics such as improved hardness and scratch-resistance and improved adhesion to various substrates. Curable gel inks can also exhibit advantages in that dot spread of the ink can be controlled, the ink does not bleed excessively into the substrate, including porous substrates.

A key component of the curable gel inks is a phase-change gelling agent (or gelator) enabling wide substrate latitude, excellent adhesion, and enhanced pigment dispersion stability. There remains a need to explore and identify new gelator molecules that are suitable for use as phase-change materials for curable inks, as thickeners for coating formations, or in other printing applications, such as 3D printing. The sharp increase in ink viscosity upon printing offers numerous advantages over non-phase change inks, namely: controlled spread (dot gain) and minimum bleed-through (jet-through) on porous substrates, wide substrate latitudes, minimal paper cockle and distortion, and the ability to rapidly build up raised print features for 3D printing without intermediate curing steps.

SUMMARY

According to embodiments illustrated herein, there is provided a bis-urea gelator having a structure of Formula I:

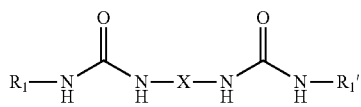

Formula I wherein R and R' each, independently of the other, is saturated aliphatic hydrocarbon group selected from the group consisting of (1) linear aliphatic groups, (2) branched aliphatic groups, (3) cyclic aliphatic groups, (4) aliphatic groups containing both cyclic and acyclic portions, any carbon atom of the saturated aliphatic hydrocarbon group may be optionally substituted with an alkyl group (cyclic or acyclic), wherein (1) and (2) groups have a carbon number of from about 1 to about 22 carbons, and wherein (3) and (4) groups have a carbon number of from about 4 to about 10 carbons; and X is selected from the group consisting of: (i) an alkylene group, (ii) an arylene group, (iii) an arylalkylene group, and (iv) an alkylarylene group.

In further embodiments, there is provided a bis-urea gelator having a structure of Formula II:

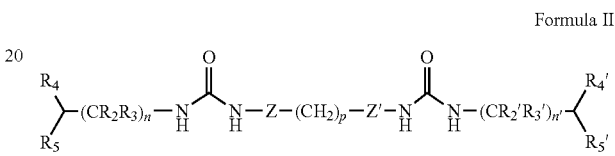

Formula II wherein each $R_2$, each $R_2'$, each $R_3$, and each $R_3'$, independently of one another, is H or $C_1$-$C_3$ alkyl; each $R_4$, each $R_4'$, each $R_5$, and each $R_5'$, independently of one another, is H or methyl; n and n' each, independently of the other, is from about 5 to from about 17; p is from about 1 to about 10; and Z and Z' each, independently of the other, is selected from the group consisting of cyclopropylene, 1,2-cyclobutylene, 1,3-cyclobutylene, cyclopentylene, 1,3-cyclopenylene, cyclohexylene, 1,3-cyclohexylene, and 1,4-cyclohexylene.

In other embodiments, there is provided an apparatus for 3-D printing comprising a bis-urea gelator having a structure of Formula I:

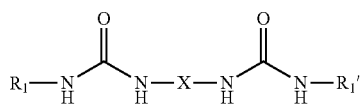

Formula I wherein R and R' each, independently of the other, saturated aliphatic hydrocarbon group selected from the group consisting of (1) linear aliphatic groups, (2) branched aliphatic groups, (3) cyclic aliphatic groups, (4) aliphatic groups containing both cyclic and acyclic portions, any carbon atom of the saturated aliphatic hydrocarbon group may be optionally substituted with an alkyl group (cyclic or acyclic), wherein (1) and (2) groups have a carbon number of from about 1 to about 22 carbons, and wherein (3) and (4) groups have a carbon number of from about 4 to about 10 carbons; and X is selected from the group consisting of: (i) an alkylene group, (ii) an arylene group, (iii) an arylalkylene group, and (iv) an alkylarylene group.

BRIEF DESCRIPTION OF THE DRAWINGS

The FIGURE illustrates generally, by way of example, but not by way of limitation, various embodiments discussed in the present document.

FIG. 1 illustrates the relationship between viscosity vs. temperature for an UV curable ink according to embodiments herein.

DETAILED DESCRIPTION

In the following description, it is understood that other embodiments may be utilized and structural and operational changes may be made without departure from the scope of the present embodiments disclosed herein.

In this specification and the claims that follow, singular forms such as "a," "an," and "the" include plural forms unless the content clearly dictates otherwise. All ranges disclosed herein include, unless specifically indicated, all endpoints and intermediate values. In addition, reference may be made to a number of terms that shall be defined as follows:

The present embodiments are directed generally to bis-urea gelators. More specifically, disclosed herein are bis-urea gelators for use in UV curable ink applications. In certain embodiments, the bis-urea gelators can be used in thickeners for coating formulations. In certain embodiments, the bis-urea gelators can be used in 3D printing. The sharp increase in ink viscosity upon printing offers numerous advantages over non-phase change inks, namely: controlled spread (dot gain) and minimum bleed-through (jet-through) on porous substrates, wide substrate latitudes, minimal paper cockle and distortion, and the ability to rapidly build up raised print features for 3D printing without intermediate curing steps.

The present embodiments provide a bis-urea gelator having the structure of Formula I:

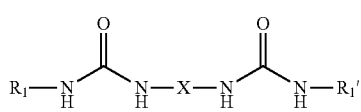

Formula I wherein $R_1$ and $R_1'$ each, independently of the other, can be a saturated aliphatic hydrocarbon group selected from the group consisting of (1) linear aliphatic groups, (2) branched aliphatic groups, and (3) cyclic aliphatic groups, (4) aliphatic groups containing both cyclic and acyclic portions, wherein any carbon atom of the saturated aliphatic hydrocarbon group may be optionally substituted with an alkyl group (cyclic or acyclic), and wherein (1) and (2) groups have a carbon number of from about 1 to about 22 carbons, from about 8 to about 20 carbons, from about 10 to about 20 carbon atoms, or from about 14 to about 18 carbon atoms, and wherein (3) and (4) groups have a carbon number of from about 4 to about 10 carbons, or from about 4 to about 8 carbons or from about 4 to about 6 carbons;

X is selected from the group consisting of: (i) an alkylene group (wherein an alkylene group is a divalent aliphatic group or alkyl group, including linear and branched, cyclic and acyclic, and substituted and unsubstituted alkylene groups, and wherein heteroatoms, such as oxygen, nitrogen, sulfur, and the like may or may not be present in the alkylene group having from about 2 carbon atom to about 24 carbon atoms, such as from about 4 carbon atom to about 20 carbon atoms, or from about 6 carbon atom to about 16 carbon atoms, (ii) an arylene group (wherein an arylene group is a divalent aryl group, including substituted and unsubstituted arylene groups) having from about 6 carbon atom to about 16 carbon atoms, such as from about 6 carbon atoms to about 12 carbon atoms or from about 6 carbon atoms to about 8 carbon atoms, (iii) an arylalkylene group (wherein an arylalkylene group is a divalent arylalkyl group, including substituted and unsubstituted arylalkylene groups, wherein the alkyl portion of the arylalkylene group can be linear or branched, and cyclic or acyclic, and wherein heteroatoms, such as oxygen, nitrogen, sulfur, and the like may or may not be present in the alkyl portion of the arylalkylene group) having from about 6 carbon atoms to about 32 carbon atoms, such as from about 6 carbon atoms to about 22 carbon atoms, or from about 6 carbon atoms to about 12 carbon atoms, and (iv) an alkylarylene group (wherein an alkylarylene group is a divalent alkylaryl group, including substituted and unsubstituted alkylarylene groups, wherein the alkyl portion of the alkylarylene group can be linear or branched, saturated or unsaturated, and cyclic or acyclic, and wherein heteroatoms, such as oxygen, nitrogen, sulfur, and the like may or may not be present in the alkyl portion of the alkylarylene group) having from about 6 carbon atoms to about 32 carbon atoms, such as from about 6 carbon atoms to about 22 carbon atoms, or from about 6 carbon atoms to about 12 carbon atoms, wherein the substituents on the substituted alkylene, arylalkylene, and alkylarylene groups can be an alkyl group, halogen, cyano, and mixtures thereof, and the like, wherein two or more substituents can be joined together to form a ring. Unlimited examples of suitable substituents for X group include:

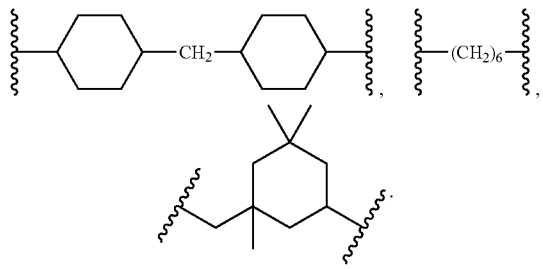

In certain embodiments, the disclosure provides a bis-urea gelator of Formula I wherein each one of $R_1$ and $R_1'$ is an unsubstituted linear aliphatic group. In other embodiments, each one of $R_1$ and $R_1'$ is a linear aliphatic group substituted with one or more $C_1$-$C_3$ alkyl, such as, methyl, ethyl, propyl, etc.

In one embodiment, $R_1$ and $R_1'$ are the same as each other; in another embodiment, $R_1$ and $R_1'$ are different from each other.

In one embodiment, $R_1$ and $R_1'$ are the same as each other.

In certain embodiments, X is an alkylene group selected from the group consisting of (1) linear aliphatic groups, (2) branched aliphatic groups, (3) cyclic aliphatic groups, (4) aliphatic groups containing both cyclic and acyclic portions, any carbon atom of the saturated aliphatic hydrocarbon group may be optionally substituted with an alkyl group (cyclic or acyclic).

In certain embodiments, X is an an alkylene group, for instance, methylene, ethylene, propylene, tetramethylene, pentamethylene, hexamethylene, heptamethylene, octamethylene, butylene group, 2-methyl propylene group, 2-methyl tetramethylene group, 2,2-dimethyl trimethylene group, 2-ethyl trimethylene group, 2-methyl pentamethylene group, 3-methyl pentamethylene group, heptamethylene group, heptylene group, octamethylene group, 2-ethyl hexylene group, nonamethylene group, decamethylene group, and the like, cyclopropylene, 1,2-cyclobutylene, 1,3-cyclobutylene, cyclopentylene, 1,3-cyclopenylene, cyclohexylene, 1,3-cyclohexylene, 1,4-cyclohexylene, or the like, any carbon atoms of the alkylene group may be substituted or unsubstituted.

In certain embodiments, X is an aliphatic group containing both cyclic and acyclic portions. In one embodiment, the aliphatic group includes one cyclic portion. In another embodiment, the aliphatic group includes one or more cyclic portions. In certain embodiments, the one or more cyclic portions may be the same or different from one another. In further embodiments, the one or more cyclic portions are separated by an acyclic portion. In further embodiments, each one of the one or more cyclic portions is independently selected from cyclopropylene, 1,2-cyclobutylene, 1,3-cyclobutylene, cyclopentylene, 1,3-cyclopenylene, cyclohexylene, 1,3-cyclohexylene, and 1,4-cyclohexylene. In certain embodiments, the acyclic portion includes a $C_1$-$C_8$ alkylene such as methylene, ethylene, propylene, butylene, pentylene, hexylene, hepylene, or octylene. In certain embodiments, both the acyclic portion and the cyclic portion are unsubstituted. In other embodiments, one or both of the acyclic portion and the cyclic portion are substituted. In certain embodiments, the one or both of the acyclic portion and the cyclic portion are substituted with one or more $C_1$-$C_3$ alkyl, such as, methyl, ethyl, propyl, and the like.

In certain embodiments, the present disclosure provides a bis-urea gelator having the structure of Formula II:

Formula II

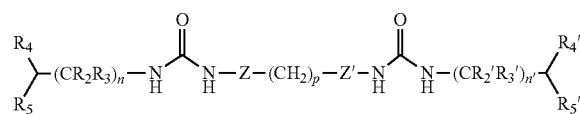

wherein each $R_2$, each $R_2'$, each $R_3$, and each $R_3'$, independently of one another, is H or $C_1$-$C_3$ alkyl, such as, methyl, ethyl, propyl, etc.; each $R_4$, each $R_4'$, each $R_5$, and each $R_5'$, independently of one another, is H or methyl; n and n' each, independently of the other, is from about 5 to from about 17, or from about 10 to from about 15; p is from about 1 to about 10, from about 1 to about 6, or from about 1 to about 4; and Z and Z' each, independently of the other, is selected from the group consisting of cyclopropylene, 1,2-cyclobutylene, 1,3-cyclobutylene, cyclopentylene, 1,3-cyclopenylene, cyclohexylene, 1,3-cyclohexylene, and 1,4-cyclohexylene; wherein at least one of Z and Z' is not null. In certain embodiments, each one of $R_2$, $R_2'$, $R_3$, and $R_3'$ are H. In certain embodiments, $R_4$ and $R_5$ are methyl. In certain embodiments, $R_4'$ and $R_5'$ are methyl.

In certain embodiments, the present disclosure provides a bis-urea gelator having the structure of Formula III:

aliphatic amine are used. A variety of isocyanates may be used in the synthesis such as, for example, hexamethylene diisocyanate (HDI), 4,4'-methylene dicyclohexyl diisocyanate (H12MDI), isophorone diisocyanate (IPDI), 1,12-diisocyanatododecane. Examples of saturated aliphatic amine include, but are not limited to stearylamine, isostearylamine, dodecylamine, and decylamine. Mixtures of linear aliphatic amines may be used in the synthesis. For example, a mixture of two saturated aliphatic amines may be used in the synthesis. When a mixture of two saturated aliphatic amines is used, the molar ratio of the saturated aliphatic amines may be at about 50:50.

Many embodiments of the compounds thus prepared can exhibit gel-like behavior in that they undergo a relatively sharp increase in viscosity over a relatively narrow temperature range when dissolved in a liquid carrier such as those compounds that behave as curable monomers when exposed to radiation such as ultraviolet light. One example of such a liquid carrier is a propoxylated neopentyl glycol diacrylate such as SR9003, commercially available from Sartomer Co. Inc. Another example of such a liquid carrier is 1,6-hexanedioldiacrylate, namely SR238, aka HDDA, commercially available from Sartomer Co. Inc.

In some embodiments, the temperature at which the ink forms the gel state is any temperature below the jetting temperature of the ink, in one embodiment any temperature that is about 5° C. or more below the jetting temperature of the ink. In one embodiment, the gel state can be formed at a temperature of at least about 25° C., at least about 30° C., or no more than about 100° C., no more than about 70° C., or no more than about 50° C., although the temperature can be outside of these ranges. A rapid and large increase in ink viscosity occurs upon cooling from the jetting temperature, at which the ink is in a liquid state, to the gel temperature, at which the ink is in the gel state. The viscosity increase is in one specific embodiment at least a $10^{25}$ fold increase in viscosity.

It has been found that optimum transfer efficiency from an intermediate transfer surface to a final recording sheet and optimum print quality can be achieved if the viscosity of the ink image deposited on the intermediate transfer member is greatly increased after jetting the ink, so as to obtain a stable and transferable image that will not smear. A suitable gelling agent for the ink will gel the monomers/oligomers in the ink vehicle quickly and reversibly and will demonstrate a narrow phase change transition, for example within a temperature range of from about 30° C. to about 100° C., or from about 30° C. to about 70° C., although the transition range can be Formula III

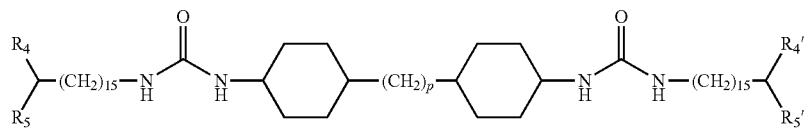

wherein each $R_4$, each $R_4'$, each $R_5$, and each $R_5'$, independently of one another, is H or methyl; p is from about 1 to about 10, from about 1 to about 6, or from about 1 to about 4. In certain embodiments, $R_4$ and $R_5$ are methyl. In certain embodiments, $R_4'$ and $R_5'$ are methyl. In certain embodiments, $R_4$ and $R_5$ are H. In certain embodiments, $R_4'$ and $R_5'$ are H.

The bis-urea gelator of the present disclosure can be synthesized by reacting an isocyanate with a saturated aliphatic amine (i.e., R—NH$_2$, R'—NH$_2$). In general, one molar equivalent of isocyanate and two molar equivalents of linear outside of these temperature ranges. The gel state of the ink in one specific embodiment exhibits a minimum of $10^{2.5}$ centipoise, and in another specific embodiment $10^3$ centipoise, increase in viscosity at transferring temperatures, e.g., in one specific embodiment from about 30 to about 70° C., compared to the viscosity at the jetting temperature. One specific embodiment is directed to gelator containing inks that rapidly increase in viscosity within from about 5° C. to about 10° C. below the jetting temperature and ultimately reach a viscosity above $10^4$ times the jetting viscosity, and in another embodiment about $10^5$ times the jetting viscosity, although the viscosity can be outside of these ranges.

When the inks are in the gel state, the viscosity of the ink is, in one embodiments, at least about 1,000 centipoise, at least about 10,000 centipoise, or at least about 100,000 centipoise, although the viscosity can be outside of these ranges. Viscosity values in the gel state are in one embodiment at least about $10^3$ centipoise, at least about $10^{4.5}$ centipoise, no more than about $10^9$ centipoise, or no more than about $10^{6.5}$ centipoise, although the gel state viscosity can be outside of these ranges. The gel phase viscosity can vary with the print process.

The gelator compositions disclosed herein can, in at least some embodiments, act as an organic gelator in an UV curable ink to the viscosity of the ink within a desired temperature range. In particular, a gelator can in some embodiments form a semi-solid gel in the ink vehicle at temperatures below the specific temperature at which the ink is jetted. Generally, a gelator composition has a viscosity of from about $10^2$ cps to about $10^6$ cps at a temperature between 85° C. to 22° C., a viscosity of from about $10^{2.5}$ cps to about $10^{5.5}$ cps at a temperature between 75 to 30° C., or a viscosity of from about $10^3$ cps to about $10^5$ cps at a temperature between 70° C. to 35° C., or a viscosity of from about $10^2$ cps to about $10^3$ cps at a temperature between 60° C. to 22° C.

Carrier Material

The ink composition includes a carrier material, or a mixture of two or more carrier materials. Examples of carrier materials include UV curable monomer, and UV curable oligomer. The curable materials are typically liquid at 25° C. The term "curable" describes, for example, a material that may be cured via polymerization, including for example free radical routes, and/or in which polymerization is photoinitiated though use of a radiation-sensitive photoinitiator. The term "UV curable" or "ultraviolet curable" refers to curing upon exposure to a ultraviolet (UV) light source, i.e., having a wavelength of 200-400 nm, and including in the presence or absence of initiators.

Curable Monomers and Oligomers

Suitable curable monomers include, but are not limited to, diacrylates, such as, propoxylated neopentyl diacrylate, e.g., SR9003, commercially available from Sartomer Co. Inc., 1,6-hexanedioldiacrylate, e.g., SR238, aka HDDA, commercially available from Sartomer; polyacrylates, such as dipentaerythritol pentaacrylate, e.g., SR399, commercially available from Sartomer Co. Inc., trimethylol propane triacrylate, pentaerythritol tetraacrylate, pentaerythritol triacrylate, dipentaerythritol pentaacrylate, glycerol propoxy triacrylate, tris(2-hydroxyethyl) isocyanurate triacrylate, pentaacrylate ester; and the like; epoxy acrylates; urethane acrylates; amine acrylates; acrylic acrylates; acrylated esters; acrylated polyesters; acrylated ethers; acrylated polyethers; and the like. Mixtures of two or more materials can also be employed as the reactive monomer. Suitable reactive monomers are commercially available from, for example, Sartomer Co., Inc., BASF Corporation, Rahn AG., and the like. In embodiments, the at least one radiation curable oligomer and/or monomer can be cationically curable, radically curable, or the like.

Specific examples of suitable acrylated oligomersinclude, but are not limited to, acrylated polyester oligomers, such as CN2262 (Sartomer Co.), EB 812 (Cytec Surface Specialties), EB 810 (Cytec Surface Specialties), CN2200 (Sartomer Co.), CN2300 (Sartomer Co.), and the like, acrylated urethane oligomers, such as EB270 (Cytec Surface Specialties), EB 5129 (Cytec Surface Specialties), CN2920 (Sartomer Co.), CN3211 (Sartomer Co.), and the like, and acrylated epoxy oligomers, such as EB 600 (Cytec Surface Specialties), EB 3411 (Cytec Surface Specialties), CN2204 (Sartomer Co.), CN110 (Sartomer Co.), and the like; and pentaerythritol tetraacrylate oligomers, such as SR399LV (Sartomer Co.) and the like.

The curable monomer or oligomer in embodiments is included in the ink in an amount of, for example, from about 20 to about 90 weight percent of the ink, such as from about 30 to about 85 weight percent, or from about 40 to about 80 weight percent by weight of the total ink composition, although the amount can be outside of these ranges. In embodiments, mixtures of curable monomer optionally with oligomer are selected to have a viscosity at 25° C. of about 1 to about 50 cP, such as about 1 to about 40 cP or about 10 to about 30 cP, although the amount can be outside of these ranges. In one embodiment, the mixture of curable monomer and oligomer has a viscosity at 25° C. of about 20 cP. Also, in some embodiments, it is desired that the curable monomer or oligomer is not a skin irritant, so that uncured ink compositions are not irritable to users.

Additives

The curable ink composition may also include one or more additives, such as but are not limited to photoinitiator, colorant, wax, cross-linking agent, additives, stabilizer and antioxidant.

Photoinitiator

The ink compositions further comprise a photoinitiator. Examples of free radical photoinitiator include benzyl ketones, monomeric hydroxyl ketones, polymeric hydroxyl ketones, α-amino ketones, acyl phosphine oxides, metallocenes, benzophenone, benzophenone derivatives, and the like. Specific examples include 1-hydroxy-cyclohexylphenylketone, benzophenone, 2-benzyl-2-(dimethylamino)-1-(4-(4-morphorlinyl)phenyl)-1-butanone, 2-methyl-1-(4-methylthio)phenyl-2-(4-morphorlinyl)-1-propanone, diphenyl-(2,4,6-trimethylbenzoyl) phosphine oxide, phenyl bis(2,4,6-trimethylbenzoyl) phosphine oxide, benzyl-dimethylketal, isopropylthioxanthone (DAROCUR ITX, available from BASF), 2,4,6-trimethylbenzoyldiphenylphosphine oxide (available as BASF LUCIRIN TPO), 2,4,6-trimethylbenzoylethoxyphenylphosphine oxide (available as BASF LUCIRIN TPO-L), bis(2,4,6-trimethylbenzoyl)-phenylphosphine oxide (available as BASF IRGACURE 819) and other acyl phosphines, 2-methyl-1-(4-methylthio)phenyl-2-(4-morphorlinyl)-1-propanone (available as BASF IRGACURE 907) and 1-(4-(2-hydroxyethoxy)phenyl)-2-hydroxy-2-methylpropan-1-one (available as BASF IRGACURE 2959), 2-benzyl 2-dimethylamino 1-(4-morpholinophenyl) butanone-1 (available as BASF IRGACURE 369), 2-hydroxy-1-(4-(4-(2-hydroxy-2-methylpropionyl)-benzyl)-phenyl)-2-methylpropan-1-one (available as BASF IRGACURE 127), 2-dimethylamino-2-(4-methylbenzyl)-1-(4-morpholin-4-ylphenyl)-butanone (available as BASF IRGACURE 379), titanocenes, isopropylthioxanthone, 1-hydroxy-cyclohexylphenylketone, 2,4,6-trimethylbenzophenone, 4-methylbenzophenone, 2,4,6-trimethylbenzoylphenylphosphinic acid ethyl ester, oligo(2-hydroxy-2-methyl-1-(4-(1-methylvinyl)phenyl) propanone), 2-hydroxy-2-methyl-1-phenyl-1-propanone, benzyl-dimethylketal, isopropyl-9H-thioxanthen-9-one, alpha amino ketone (IRGACURE 379), oligo[2-hydroxy-2-methyl-1-[4-(1-methylvinyl)phenyl]propanone] (available as Esacure KIP 150 from Lamberti); and the like, as well as mixtures thereof.

Optionally, the curable inks can also contain an amine synergist, which are co-initiators which can donate a hydrogen atom to a photoinitiator and thereby form a radical species that initiates polymerization, and can also consume dissolved oxygen, which inhibits free-radical polymerization, thereby increasing the speed of polymerization. Examples of suitable amine synergists include (but are not limited to) ethyl-4-dimethylaminobenzoate, 2-ethylhexyl-4-dimethylaminobenzoate, and the like, as well as mixtures thereof.

Initiators for inks disclosed herein can absorb radiation at any desired or effective wavelength, in one embodiment at least about 200 nanometers, and in one embodiment no more than about 560 nanometers, and in another embodiment no more than about 420 nanometers, although the wavelength can be outside of these ranges.

The initiator can be present in the ink in any desired or effective amount, in one embodiment at least about 0.5 percent by weight of the carrier, and in another embodiment at least about 1 percent by weight of the carrier, and in one embodiment no more than about 15 percent by weight of the carrier, and in another embodiment no more than about 10 percent by weight of the carrier, although the amount can be outside of these ranges.

Colorants

The UV curable ink according to the present disclosure may be produced as a colored ink by adding a colorant during ink production. Alternatively, an UV curable ink lacking a colorant may be printed on a substrate during a first pass, followed by a second pass. For example, each UV curable ink can be stored in a separate reservoir. The printing system delivers each ink separately to the substrate, and the two inks interact. The UV curable inks may be delivered to the substrate simultaneously or consecutively. Any desired or effective colorant can be employed in the ink compositions, including pigment, dye, mixtures of pigment and dye, mixtures of pigments, mixtures of dyes, and the like.

Any suitable colorant may be used in embodiments herein, including dyes, pigments, or combinations thereof. As colorants, examples may include any dye or pigment capable of being dispersed or dissolved in the vehicle. Examples of suitable pigments include, for example, Paliogen Violet 5100 (BASF); Paliogen Violet 5890 (BASF); Heliogen Green L8730 (BASF); Lithol Scarlet D3700 (BASF); SUNFAST® Blue 15:4 (Sun Chemical 249-0592); HOSTAPERM Blue B2G-D (Clariant); Permanent Red P-F7RK; HOSTAPERM Violet BL (Clariant); Lithol Scarlet 4440 (BASF); Bon Red C (Dominion Color Company); Oracet Pink RF (Ciba); Paliogen Red 3871 K (BASF); SUNFAST® Blue 15:3 (Sun Chemical 249-1284); Paliogen Red 3340 (BASF); SUNFAST® Carbazole Violet 23 (Sun Chemical 246-1670); Lithol Fast Scarlet L4300 (BASF); Sunbrite Yellow 17 (Sun Chemical 275-0023); Heliogen Blue L6900, L7020 (BASF); Sunbrite Yellow 74 (Sun Chemical 272-0558); SPECTRA PAC® C Orange 16 (Sun Chemical 276-3016); Heliogen Blue K6902, K6910 (BASF); SUNFAST® Magenta 122 (Sun Chemical 228-0013); Heliogen Blue D6840, D7080 (BASF); Sudan Blue OS (BASF); Neopen Blue FF4012 (BASF); PV Fast Blue B2G01 (Clariant); Irgalite Blue BCA (Ciba); Paliogen Blue 6470 (BASF); Sudan Orange G (Aldrich); Sudan Orange 220 (BASF); Paliogen Orange 3040 (BASF); Paliogen Yellow 152, 1560 (BASF); Lithol Fast Yellow 0991 K (BASF); Paliotol Yellow 1840 (BASF); Novoperm Yellow FGL (Clariant); Lumogen Yellow D0790 (BASF); Suco-Yellow L1250 (BASF); Suco-Yellow D1355 (BASF); Suco Fast Yellow DI 355, DI 351 (BASF); Hostaperm Pink E 02 (Clariant); Hansa Brilliant Yellow 5GX03 (Clariant); Permanent Yellow GRL 02 (Clariant); Permanent Rubine L6B 05 (Clariant); Fanal Pink D4830 (BASF); Cinquasia Magenta (Du Pont), Paliogen Black L0084 (BASF); Pigment Black K801 (BASF); and carbon blacks such as REGAL 330™ (Cabot), Carbon Black 5250, Carbon Black 5750 (Columbia Chemical), mixtures thereof and the like. Examples of suitable dyes include Usharect Blue 86 (Direct Blue 86), available from Ushanti Color; Intralite Turquoise 8GL (Direct Blue 86), available from Classic Dyestuffs; Chemictive Brilliant Red 7BH (Reactive Red 4), available from Chemiequip; Levafix Black EB, available from Bayer; Reactron Red H8B (Reactive Red 31), available from Atlas Dye-Chem; D&C Red #28 (Acid Red 92), available from Warner-Jenkinson; Direct Brilliant Pink B, available from Global Colors; Acid Tartrazine, available from Metrochem Industries; Cartasol Yellow 6GF Clariant; Carta Blue 2GL, available from Clariant; and the like. Example solvent dyes include spirit soluble dyes such as Neozapon Red 492 (BASF); Orasol Red G (Ciba); Direct Brilliant Pink B (Global Colors); Aizen Spilon Red C-BH (Hodogaya Chemical); Kayanol Red 3BL (Nippon Kayaku); Spirit Fast Yellow 3G; Aizen Spilon Yellow C-GNH (Hodogaya Chemical); Cartasol Brilliant Yellow 4GF (Clariant); Pergasol Yellow CGP (Ciba); Orasol Black RLP (Ciba); Savinyl Black RLS (Clariant); Morfast Black Conc. A (Rohm and Haas); Orasol Blue GN (Ciba); Savinyl Blue GLS (Sandoz); Luxol Fast Blue MBSN (Pylam); Sevron Blue 5GMF (Classic Dyestuffs); Basacid Blue 750 (BASF), Neozapon Black X51 [C.I. Solvent Black, C.I. 12195] (BASF), Sudan Blue 670 [C.I. 61554] (BASF), Sudan Yellow 146 [C.I. 12700] (BASF), Sudan Red 462 [C.I. 260501] (BASF), mixtures thereof and the like.

The colorant is present in the curable ink in any desired or effective amount to obtain the desired color or hue, in embodiments from about 0.1 percent to about 15 percent by weight of the ink, or from about 0.2 percent to about 8 percent by weight of the ink, although the amount can be outside of these ranges.

Wax

The curable ink further contains at least one wax. The wax can be curable or non-curable. The wax may be any wax component that is miscible with the other ink components. Inclusion of the wax promotes an increase in viscosity of the ink as it cools from the jetting temperature.

Desirably, the wax composition is curable so as to participate in the curing of the ink. Suitable examples of curable waxes include those that are functionalized with curable groups. The curable groups may include, for example, acrylate, methacrylate, alkene, allylic ether, epoxide and/or oxetane groups. These waxes can be synthesized by the reaction of a wax equipped with a transformable functional group, such as carboxylic acid, hydroxyl and the like. The functionalized wax is also able to participate in the ultraviolet light initiated cure and thus does not lower the final robustness of the image. Additionally, the wax acts as a binder, preventing syneresis, and in printing, acts as a barrier or coating on paper/image receiving substrate, preventing the principle carrier from wicking or showing through the paper. The curable wax also reduces haloing tendency.

In embodiments, the optional curable wax is included in the ink in an amount of from, for example, about 1 to about 25% by weight of the ink, such as from about 2 to about 20% by weight of the ink, or from about 2.5 to about 15% by weight of the ink.

Antioxidant

The ink composition can also optionally contain an antioxidant. The optional antioxidants of the ink compositions protect the images from oxidation and also protect the ink components from oxidation during the heating portion of the ink preparation process. Specific examples of suitable antioxidants include NAUGUARD® series of antioxidants such as NAUGUARD® 445, NAUGUARD® 524, NAUGUARD® 76, and NAUGUARD® 5112 (commercially available from Chemtura Corporation, Philadelphia, Pa.), the IRGANOX® series of antioxidants such as IRGANOX® 10310 (commercially available from BASF), IRGASTAB® UV10 (commercially available from Ciba Specialty Chemicals), and the like. When present, the optional antioxidant can be present in the ink in any desired or effective amount, such as in an amount of from at least about 0.01 to about 20 percent by weight of the ink, such as about 0.1 to about 5 percent by weight of the ink, or from about 1 to about 3 percent by weight of the ink, although the amount can be outside of these ranges.

Preparation of Ink

The ink composition of the present disclosure can be prepared by any desired or suitable method. For example, in the case of curable gel UV inks the ink ingredients can be mixed together, followed by heating, typically to a temperature of from about 50° C. to about 100° C., although the temperature can be outside of this range, and stirring until a homogeneous ink composition is obtained, followed by cooling the ink to ambient temperature (typically from about 20° C. to about 25° C.). In the case of liquid ink compositions, the ink ingredients can simply be mixed together with stirring to provide a homogeneous composition, although heating can also be used if desired or necessary to help form the composition. Other methods for making ink compositions are known in the art and will be apparent based on the present disclosure.

Printing of the Ink

The curable ink may generally be printed on a suitable substrate such as, without limitation, paper, glass art paper, bond paper, paperboard, Kraft paper, cardboard, semi-synthetic paper or plastic sheets, such as polyester or polyethylene sheets, and the like. These various substrates can be provided in their natural state, such as uncoated paper, or they can be provided in modified forms, such as coated or treated papers or cardboard, printed papers or cardboard, and the like.

Specific suitable papers include plain papers such as XEROX 4200 papers, XEROX Image Series papers, ruled notebook paper, bond paper, silica coated papers such as Sharp Company silica coated paper, JuJo paper, HAMMERMILL LASERPRINT paper, and the like, glossy coated papers such as XEROX Digital Color Gloss, Sappi Warren Papers LUSTROGLOSS, specialty papers such as Xerox DURAPAPER, and the like.

Further suitable materials may be used, including but not limited to, transparency materials, fabrics, textile products, plastics, polymeric films, inorganic recording mediums such as metals and wood, and the like, transparency materials, fabrics, textile products, plastics, polymeric films, inorganic substrates such as metals and wood, and the like.

The inks described herein are further illustrated in the following examples. All parts and percentages are by weight unless otherwise indicated.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The examples set forth herein below and are illustrative of different compositions and conditions that can be used in practicing the present embodiments. All proportions are by weight unless otherwise indicated. It will be apparent, however, that the present embodiments can be practiced with many types of compositions and can have many different uses in accordance with the disclosure above and as pointed out hereinafter.

Example 1

Synthesis of Bis-Urea Gelators

Compound 1

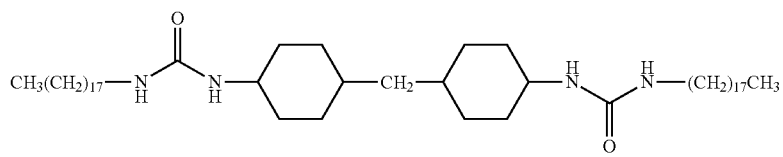

Into a solution containing Desmodur W (H12MDI, 4.91 g, 18.70 mmol; obtained from Bayer) and hexane (40 milliliters) with stirring at room temperature was added stearylamine (10.08 g, 37.4 mmol; obtained from Sigma-Aldrich Fine Chemicals). The resulting solution was heated to reflux for 1 hour. The IR spectrum indicated that all isocyanate was consumed. The solution was cooled to room temperature during which a white fluffy precipitate was formed. The product was filtered on a Buchner funnel and the filtercake was washed with hexanes and dried on a vacuum pump to furnish 15 g (18.7 mmol, 100% yield) of a white fluffy solid.

Compound 2

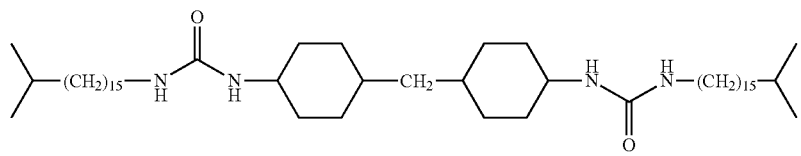

Compound 2 is prepared according to the same procedure as compound 1 except that isostearylamine is used in place of stearylamine.

Example 2

Gelation Test 5 weight percent of Compound 1 was dissolved in acrylate monomer (SR003, propoxylated neopentyl glycol diacrylate; or SR238, 1,6-hexanedioldiacrylate, aka HDDA) and heated to 90° C. for 30 minutes. The mixture was cooled to room temperature and checked for gelation behavior. Compound 1 formed a gel in either SR9003 or HDDA, both are suitable ink vehicles for UV curable inks.

Example 3

Preparation of Cyan Pigment Dispersion

To a 4 L jacketed stainless steel container was added SR9003 (1166.2 g) and EFKA (BASF dispersant, 993.8 g of a 32.4 solids in SR9003). This was stirred using a high speed mixer and to this was added cyan pigment (SUN spectrapac, 540 g) over 1 hour. The mixer was replaced with a basket mill (Hockmeyer, 0.1 mm screan) containing Zirconium beads (0.3 mm, 40 g) and the RPM was increased to 5500 over 5 minutes while cooling the jacketed reactor. Upon reaching 5500 rpm the basket mill was operated for 3 hours while maintaining a reaction temperature of 90° C. The basket mill was raised and the dispersion was discharged to afford a cyan dispersion of 20% solids content.

Example 4

General Procedure for Ink Formation

To a 20 mL amber glass vial was added 1.0 g Compound 1, 0.4 g Unilin 350-acrylate (reactive wax phase change agent, derived from UNILIN 350, which is available from Baker Petrolite), 14.1 SR9003 or SR238 monomer, 1.0 g SR399LV, 0.6 g Irgacure 379 (an α-amino ketone photoinitiator, available from Ciba Specialty Chemicals, Inc.), 0.1 g Irgacure 819, 0.8 g Esacure KIP150, 0.04 g and Irgastab UV10 (an ultraviolet photoinitiator, available from Ciba Specialty Chemicals, Inc.), and 20% Cyan pigment concentrate dispersion in SR9003. The mixture was stirred with a magnetic stir bar and heated to 90° C. for 1 hour to form a clear solution (the ink base). To the hot ink base was added a pigment dispersion concentrate (15 wt % Cyan pigment in SR9003 monomer) and the resulting mixture was heated with stirring for an additional hour at 90° C.

It is understood that when selecting specific amounts for individual ink components, the sum of all the components in the final ink adds to 100%.

TABLE 1

(Ink with Gelator 1)

| Component | Weight % | m/g |
|---|---|---|
| Compound 1 | 5.00 | 1.0 |
| Unilin 350-acrylate | 2.00 | 0.4 |
| SR238 monomer | 70.30 | 14.1 |
| SR399LV | 5.00 | 1.0 |
| Irgacure 379 | 3.00 | 0.6 |
| Irgacure 819 | 0.50 | 0.1 |
| Esacure KIP150 | 4.00 | 0.8 |
| Irgastab UV10 | 0.20 | 0.04 |
| 20 wt % Cyan pigment dispersion in SR9003 | 10.00 | 2.0 |
| TOTAL | 100.0 | 20.0 |

Example 5

Rheology of Ink Containing Bis-Urea Gelators

Temperature dependent complex viscosity of an ink containing the bis-urea gelator was measured. The data was measured using a controlled-strain rheometer from TA Instruments (RFS-3) at a constant frequency of 1 Hz. The bis-urea gelators can cover a wide scope of viscosity ranges, and can be tuned for optimum phase change temperature and ultimate viscosity at room temperature, which can be advantageous for non-contact leveling of our inks, or for printing of 3D objects, for example. Table 2 summarizes the viscosity data for the Cyan ink in Example 4.

TABLE 2

Temperature/Time Viscosity Data for Cyan Ink (Example 4 - Ink with Gelator 1)

| Temp/° C. | Complex Viscosity/cps | G'/Pa | G"/Pa | Tan delta |
|---|---|---|---|---|
| 90 | 2.41 | 0.001249 | 0.015098 | 12.08498 |
| 85 | 2.75 | 0.001048 | 0.017274 | 16.48775 |
| 80 | 2.97 | 0.001318 | 0.018631 | 14.14031 |
| 75 | 3.27 | 0.000937 | 0.020524 | 21.89315 |
| 70 | 4.38 | 0.001531 | 0.027483 | 17.95013 |
| 65 | 5.90 | 0.001716 | 0.037045 | 21.58704 |

TABLE 2-continued

Temperature/Time Viscosity Data for Cyan Ink (Example 4 - Ink with Gelator 1)

| Temp/° C. | Complex Viscosity/cps | G'/Pa | G''/Pa | Tan delta |
|---|---|---|---|---|
| 60 | 9.11 | 0.003176 | 0.057153 | 17.99729 |
| 55 | 15.2 | 0.008206 | 0.09515 | 11.59553 |
| 50 | 25.14 | 0.016647 | 0.157096 | 9.436766 |
| 45 | 45.53 | 0.038269 | 0.283479 | 7.407627 |
| 40 | 87.49 | 0.089339 | 0.542418 | 6.071439 |
| 35 | 167.07 | 0.192829 | 1.031884 | 5.351281 |
| 30 | 318.93 | 0.399234 | 1.963686 | 4.918634 |

All the patents and applications referred to herein are hereby specifically, and totally incorporated herein by reference in their entirety in the instant specification.

What is claimed is:

1. A bis-urea gelator having a structure of Formula I:

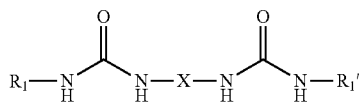

Formula I wherein $R_1$ and $R_1'$ are different from each other, and each independently of the other, is saturated aliphatic hydrocarbon group selected from the group consisting of (1) linear aliphatic groups, (2) branched aliphatic groups, (3) cyclic aliphatic groups, (4) aliphatic groups containing both cyclic and acyclic portions, any carbon atom of the saturated aliphatic hydrocarbon group may be optionally substituted with an alkyl group (cyclic or acyclic), wherein (1) and (2) groups have a carbon number of from 14 to 18 carbons, and wherein (3) and (4) groups have a carbon number of from 4 to 10 carbons; and X is an aliphatic group containing both cyclic and acyclic portions, any carbon atom of the aliphatic hydrocarbon group may be optionally substituted with an alkyl group (cyclic or acyclic).

2. A bis-urea gelator having a structure of Formula I:

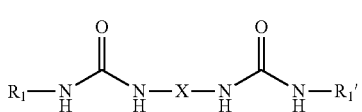

Formula I wherein each one of $R_1$ and $R_1'$ is a linear aliphatic group containing from 14 to 18 carbon atoms substituted with one or more $C_1$-$C_3$ alkyl; and X is an aliphatic group containing both cyclic and acyclic portions, any carbon atom of the aliphatic hydrocarbon group may be optionally substituted with an alkyl group (cyclic or acyclic).

3. The gelator according to claim 2, wherein $R_1$ and $R_1'$ are the same as each other.

4. The gelator according to claim 2, wherein each one of the one or more cyclic portions is independently selected from the group consisting of cyclopropylene, 1,2-cyclobutylene, 1,3-cyclobutylene, cyclopentylene, 1,3-cyclopenylene, cyclohexylene, 1,3-cyclohexylene, and 1,4-cyclohexylene.

5. The gelator according to claim 2, wherein the acyclic portion comprises a $C_1$-$C_8$ alkylene.

6. A bis-urea gelator having a structure of Formula II:

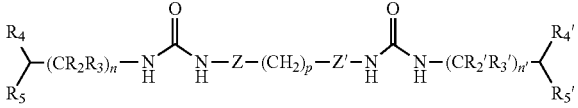

Formula II wherein each $R_2$ each $R_2'$ each $R_3$ and each $R_3'$, independently of one another is H or $C_1$-$C_3$ alkyl; $R_4$, $R_4'$, $R_5$, and $R_5'$ are methyl; n and n' each, independently of the other, is from 10 to 15; p is from 1 to 10; and Z and Z' each, independently of the other, is selected from the group consisting of null, cyclopropylene, 1,2-cyclobutylene, 1,3-cyclobutylene, cyclopentylene, 1,3-cyclopenylene, cyclohexylene, 1,3-cyclohexylene, and 1,4-cyclohexylene, wherein at least one of Z and Z' is not null.

7. The gelator according to claim 6, wherein the Z and Z' are each 1,4-cyclohexylene and p is from 1 to 4.

8. The gelator according to claim 6, wherein the each one of the one or more cyclic portions is 1,4-cyclohexylene.

9. The gelator according to claim 6, wherein the acyclic portion is methylene.

10. The gelator according to claim 6, wherein at least one of Z and Z' is not null.

11. A bis-urea gelator having a structure of Formula III:
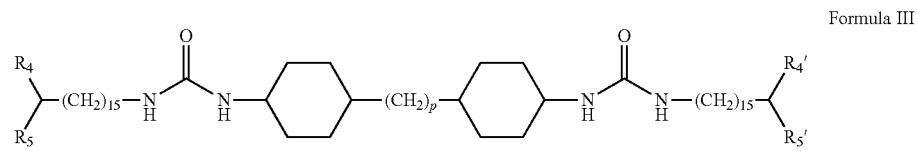
Formula III
wherein $R_4$, $R_4'$, $R_5$, and $R_5'$ are methyl; and p is from 1 to 10.
12. The gelator according to claim 6, p is 1.
* * * * *